United States Patent
Pan et al.

(10) Patent No.: US 10,729,633 B2
(45) Date of Patent: *Aug. 4, 2020

(54) METHODS FOR BOOSTING UVA PHOTO-PROTECTION USING ANTIOXIDANTS

(71) Applicant: L'OREAL, Paris (FR)

(72) Inventors: Zhi Pan, Ridgewood, NJ (US); Anne-Laure Suzanne Bernard, New-York, NY (US); Yang Deng, Green Brook, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/939,422

(22) Filed: Mar. 29, 2018

(65) Prior Publication Data

US 2019/0298638 A1 Oct. 3, 2019

(51) Int. Cl.

| | | |
|---|---|---|
| *A61K 8/34* | (2006.01) | |
| *A61K 8/35* | (2006.01) | |
| *A61K 8/365* | (2006.01) | |
| *A61K 8/60* | (2006.01) | |
| *A61Q 17/04* | (2006.01) | |
| *A61K 8/36* | (2006.01) | |
| *A61K 8/37* | (2006.01) | |
| *A61K 8/40* | (2006.01) | |
| *A61K 8/49* | (2006.01) | |
| *A61K 8/86* | (2006.01) | |
| *A61K 8/891* | (2006.01) | |
| *A61K 8/895* | (2006.01) | |

(52) U.S. Cl.
CPC .............. *A61K 8/602* (2013.01); *A61K 8/347* (2013.01); *A61K 8/35* (2013.01); *A61K 8/36* (2013.01); *A61K 8/365* (2013.01); *A61K 8/37* (2013.01); *A61K 8/40* (2013.01); *A61K 8/4926* (2013.01); *A61K 8/4953* (2013.01); *A61K 8/86* (2013.01); *A61K 8/891* (2013.01); *A61K 8/895* (2013.01); *A61Q 17/04* (2013.01); *A61K 2800/30* (2013.01); *A61K 2800/48* (2013.01); *A61K 2800/49* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 10,137,072 B2* | 11/2018 | Pan | A61K 8/602 |
| 2014/0170090 A1 | 6/2014 | Thaggard | |
| 2016/0106654 A1* | 4/2016 | Lewis, II | A61K 8/447 424/59 |
| 2016/0367470 A1* | 12/2016 | Chiou | A61Q 17/04 |
| 2017/0281499 A1* | 10/2017 | Pan | A61K 8/498 |
| 2017/0281503 A1* | 10/2017 | Pan | A61K 8/602 |
| 2017/0281504 A1* | 10/2017 | Pan | A61K 8/602 |
| 2017/0281505 A1* | 10/2017 | Pan | A61K 8/602 |

FOREIGN PATENT DOCUMENTS

| | | | |
|---|---|---|---|
| FR | 2795319 A1 | 12/2000 | |
| WO | WO-2013/004777 A1 | 1/2013 | |
| WO | WO-2016/166345 A1 | 10/2016 | |

OTHER PUBLICATIONS

International Search Report and Written Opinion dated Jun. 4, 2019 for corresponding PCT Application No. PCT/US2019/023963.
Matsui, Mary S. et al., "Non-Sunscreen Photoprotection: Antioxidants Add Value to a Sunscreen," Journal of Investigative Dermatology Symposium Proceedings, vol. 14, No. 1, 2009, pp. 56-59 XP055589522.
Oresajo, C. et al., "Protective effects of a topical antioxidant mixture containing vitamin C, ferulic acid, and phloretin against ultraviolet-induced photodamage in human skin," Journal of Cosmetic Dermato, Blackwell Science, Oxford, GB, vol. 7, No. 4, 2008, pp. 290-297 XP008105375.

* cited by examiner

*Primary Examiner* — Brian Gulledge
(74) *Attorney, Agent, or Firm* — Polsinelli PC

(57) ABSTRACT

Methods for providing broad spectrum photo protection to skin using antioxidants that provide UVA protection to skin are described. The methods include topically applying a cosmetic composition comprising: (a) at least one antioxidant having an Oxygen Radical Absorbance Capacity (ORAC) of at least 10,000 µmol TE/g and a Hydroxyl Radical Absorbance Capacity (HORAC) of at least 2,600 µmol GAE/g; (b) at least one organic UV filter; and (c) a cosmetically acceptable carrier; wherein the cosmetic composition provides an increase in $UVA_{PPD}$ PF of at least 30% relative to an otherwise identical cosmetic composition without the antioxidant(s) of (a). The disclosure also relates to the cosmetic compositions useful in the described methods.

19 Claims, 1 Drawing Sheet

METHODS FOR BOOSTING UVA PHOTO-PROTECTION USING ANTIOXIDANTS

FIELD OF THE DISCLOSURE

The instant disclosure relates to methods and compositions for boosting UVA photo-protection using antioxidants to provide broad spectrum photo protection to skin.

BACKGROUND

Most individuals are exposed to large amounts of ultraviolet (UV) radiation throughout their lifetimes due primarily to sunlight exposure. Sunlight includes two types of UV rays: long wave ultraviolet A (UVA) and short wave ultraviolet B (UVB), both of which can damage skin. UVA rays account for up to 95 percent of the UV radiation reaching the Earth's surface. Although they are less intense than UVB rays, UVA rays are 30 to 50 times more prevalent. They are present with relatively equal intensity during all daylight hours throughout the year, and can penetrate clouds and glass.

UVA rays penetrate the skin more deeply than UVB rays and have long been known to play a major part in skin aging and wrinkling (photo-aging), but until recently scientists believed that UVA rays did not cause significant damage to the epidermis (outermost skin layer) where most skin cancers occur. Studies over the past two decades, however, show that UVA radiation damages skin cells called keratinocytes in the basal layer of the epidermis.

Both UVA and UVB radiation contribute to skin damage that accelerates the appearance of aging, for example, loss of skin elasticity and the appearance of wrinkles. This process is commonly referred to as photo-aging. As skin ages, the outer skin layer (epidermis) thins, even though the number of cells remain largely unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity, which becomes more noticeable in sun-exposed areas (solar elastosis). Elastosis produces the leathery, weather-beaten appearance common to farmers, sailors, and others who spend a large amount of time outdoors.

Due to the need for protection from both UVA and UVB radiation, sunscreen products designated as "broad spectrum sunscreens" have been developed. Sunscreen products that are labeled as "broad spectrum" provide protection from both UVA and UVB radiation; and in the United States these products must meet specific requirements set by the Food and Drug Administration (FDA). The number of known UVA filters and especially FDA approved UVA filters is small and therefore products are limited in what UVA filters can be used to provide broad spectrum protection.

SUMMARY OF THE DISCLOSURE

The instant disclosure relates to methods and compositions for providing broad spectrum photo protection to skin, i.e., protection from both UVA and UVB radiation. The inventors unexpectedly discovered that certain antioxidants boost the UVA protection provided by UV filters and can therefore be used in cosmetic compositions to increase photo-protection from UVA radiation. Certain antioxidants synergistically interact with UV filters to significantly boost the UVA protection provided by the UV filters. The antioxidants that boost UVA photo-protection can be combined with UV filters (e.g., organic UVA and UVB filters) to provide cosmetic compositions (such as sunscreen compositions) that provide a higher level UVA protection that cannot be achieved by UV filters alone. Also, because the antioxidants can be used together with organic UV filters to boost the overall UVA protection provided by the sunscreen composition, the total amount of UVA filters needed to attain a desired degree of UVA protection can be reduced.

Methods according to the instant disclosure for providing broad spectrum photo-protection to skin can be carried out by applying to the skin a cosmetic composition comprising: (a) at least one antioxidant that boosts photo-protection from UVA radiation having an Oxygen Radical Absorbance Capacity (ORAC) of at least 10,000 mol TE/g and a Hydroxyl Radical Absorbance Capacity (HORAC) of at least 2,600 mol GAE/g; (b) at least one organic UV filter; and (c) a cosmetically acceptable carrier; wherein the cosmetic composition provides an increase in $UVA_{PPD}$ PF of at least 30% relative to an otherwise identical cosmetic composition without the antioxidant(s) of (a). The method typically provides an increase in $UVA_{PPD}$ PF of at least 30% relative to an otherwise identical cosmetic composition without the antioxidant(s). In some instances, it may be preferable that the at least one antioxidant of (a) additionally have a Superoxide Radical Absorbance Capacity (SORAC) of less than 200 U/mg.

Non-limiting examples of antioxidants that boost photo-protection from UVA radiation include polydatin, phloretin, resveratrol, ferulic acid, and a mixture thereof. One of more of these antioxidants is combined with one or more UV filters, in particular organic UV filters, in a cosmetically acceptable carrier. The UV filter(s) may be UVB filters, UVA filters (UVA1 and/or UVA2 filters), and/or inorganic UV filters (UVA and/or UVB filters).

Non-limiting examples of UV filters include a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof. Many organic UVB filters are known and are more common than UVA filters. UVA filters include, but are not limited to, avobenzone (UVA1), ecampsulate (MEXORYL SX) (UVA2), and meradimate (menthyl anthranilate). Filters such as dioxybenzone, oxybenzone, and sulisobenzone provide both UVB and UVA2 protection.

The cosmetic compositions often include one or more additional components such as solubilizing agents, emulsifiers, silicone compounds, thickening agent, fatty compounds, fillers, preservatives, etc.

In addition to providing broad spectrum photo-protection, the cosmetic compositions are useful in methods for providing anti-aging benefits to skin; whitening or preventing darkening of skin; improving the appearance of skin; strengthening skin's natural antioxidant defenses; diminishing the visible signs of skin aging; and improving skin's radiance and firmness.

Figure 1:
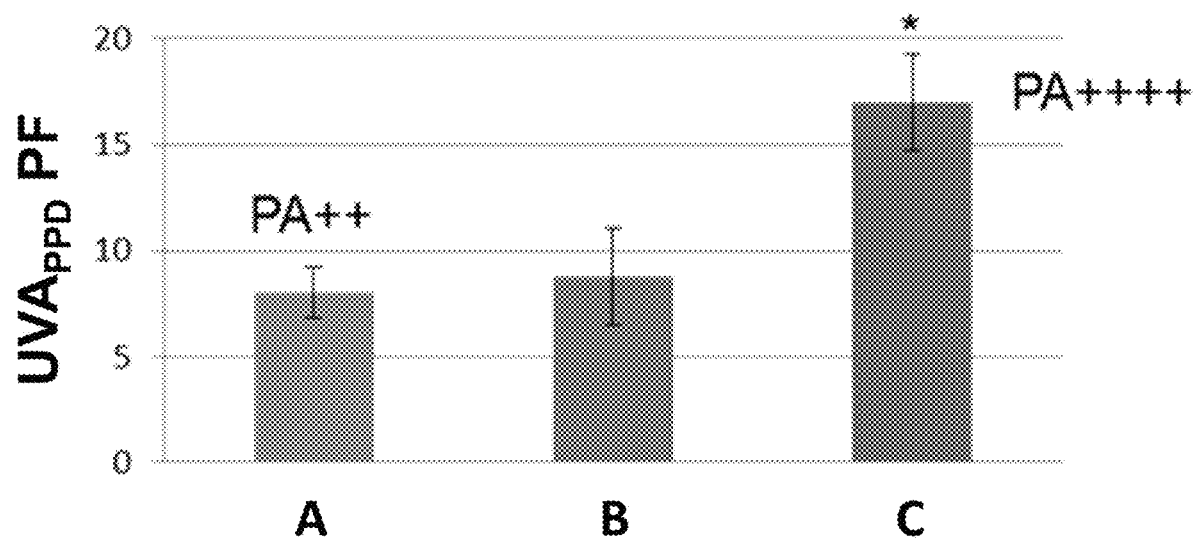
FIG. 1 is a graph showing: (A) the $UVA_{PPD}$ PF of a cosmetic composition comprising UV filters but no antioxidants that boost UVA photo-protection; (B) a cosmetic composition comprising UV filters and baicalin; and (C) a cosmetic composition comprising UV filters and polydatin.

It should be understood that the various aspects of the present disclosure are not limited to the arrangements and instrumentality shown in the figures.

DETAILED DESCRIPTION OF THE DISCLOSURE

The methods and cosmetic compositions of the present disclosure provide broad spectrum photo-protection from UV radiation. The term "broad spectrum photo-protection" means photo-protection from both UVA and UVB radiation. Sun Protection Factor (SPF) indicates a sunscreen's ability to protect against UVB rays but does not adequately designate to what extent (if any) a sunscreen composition protects against UVA radiation. SPF is a measure of how much solar energy (UV radiation) is required to produce sunburn on protected skin (i.e., in the presence of sunscreen) relative to the amount of solar energy required to produce sunburn on unprotected skin. As the SPF value increases, sunburn protection increases. There is a popular misconception that SPF relates to time of solar exposure. For example, many consumers believe that, if they normally get sunburn in one hour, then an SPF 15 sunscreen allows them to stay in the sun 15 hours (i.e., 15 times longer) without getting sunburn. This is not true because SPF is not directly related to time of solar exposure but to amount of solar exposure. Although solar energy amount is related to solar exposure time, there are other factors that impact the amount of solar energy. For example, the intensity of the solar energy impacts the amount.

To characterize protection from UVA radiation, the PPD (Persistent Pigment Darkening) method, which measures the color of the skin observed 2 to 4 hours after exposure of the skin to UVA radiation, is used. This method was adopted in 1996 by the Japanese Cosmetic Industry Association (JCIA) as the official test procedure for the UVA labelling of products and is commonly used in industry, especially in Europe and the United States. See JAPAN COSMETIC INDUSTRY ASSOCIATION TECHNICAL BULLETIN, *Measurement Standards for UVA Protection Efficacy*. Issued Nov. 21, 1995 and effective of Jan. 1, 1996), which is incorporated herein by reference in its entirety.

The UVA protection factor based on Persistent Pigment Darkening (PPD) is designated as "$UV\text{-}A_{PPD}$ PF" and is expressed mathematically by the ratio of the dose of UVA radiation necessary to reach the pigmentation threshold with the UV screening agent ($MPPD_p$) to the dose of UVA radiation necessary to reach the pigmentation threshold without UV screening agent ($MPPD_{np}$), as shown below.

$$UVA_{ppd}PF = \frac{MPPD_p}{MPPD_{np}}$$

The methods of the present disclosure provide broad spectrum photo-protection to skin by topically applying to the skin a cosmetic composition comprising:

(a) at least one antioxidant that boosts UVA photo-protection having:
  i. an Oxygen Radical Absorbance Capacity (ORAC) of at least 10,000 µmol TE/g; and
  ii. a Hydroxyl Radical Absorbance Capacity (HORAC) of at least 2,600 µmol GAE/g;
(b) at least one organic UV filter; and
(c) a cosmetically acceptable carrier;
wherein the cosmetic composition provides an increase in $UVA_{PPD}$ PF of at least 30% relative to an otherwise identical cosmetic composition without the antioxidant(s) of (a). In some instances, the at least one antioxidant of (a) may have a Superoxide Radical Absorbance Capacity (SORAC) of less than 200 U/mg.

The cosmetic compositions comprising the antioxidant(s) that boosts photo-protection from UVA radiation increase the in $UVA_{PPD}$ PF of the cosmetic composition by at least 40, 50, 60, 70, 80, 90, 100, 110, 120, 130, 140, 150, 160, 170, 180, 190, or 200%, relative to an otherwise identical cosmetic composition without the antioxidant(s). A maximum percent increase in $UVA_{PPD}$ PF may be 100, 120, 150, 180, 200, 220, 250, 270, or 300% (e.g., the percent increase in $UVA_{PPD}$ PF may be from at least 30% to 300%, relative to an otherwise identical cosmetic composition without the antioxidant(s)).

Not all antioxidants that boost UVA protection provide the same degree of boosting. Therefore, the increase in $UVA_{PPD}$ PF provided by the cosmetic compositions of the present disclosure can vary depending on the antioxidant(s) included in the compositions. Non-limiting examples of antioxidants that boost UVA protection include polydatin, phloretin, resveratrol, ferulic acid, their derivatives, and mixtures thereof.

The degree of increase (boost) in UVA protection provided by each of these antioxidants can vary and therefore the $UVA_{PPD}$ PF of cosmetic compositions comprising them may vary.

A cosmetic composition comprising polydatin may provide an increase in $UVA_{PPD}$PF of at least 150% relative to an otherwise identical cosmetic composition without polydatin. In some instances, a cosmetic composition comprising polydatin may provide an increase in $UVA_{PPD}$ PF of at least 150, 160, 170, 180, 190, 200%, relative to an otherwise identical cosmetic composition without polydatin. A maximum percent increase in $UVA_{PPD}$ PF when the cosmetic composition includes polydatin may be 230, 250, 270, or 300% (e.g., the percent increase by be from at least 150% to 300%, relative to an otherwise identical cosmetic composition without polydatin).

A cosmetic composition comprising phloretin may provide an increase in $UVA_{PPD}$PF of at least 50% relative to an otherwise identical cosmetic composition without phloretin. In some instances, a cosmetic composition comprising phloretin may provide an increase in $UVA_{PPD}$ PF of at least 55, 60, 65, 70, or 75% relative to an otherwise identical cosmetic composition without phloretin. A maximum percent increase in $UVA_{PPD}$ PF when the cosmetic composition includes phloretin may be 75, 80, 85, 90, 95, or 100% (e.g., the percent increase by be from at least 50% to 100%, relative to an otherwise identical cosmetic composition without phloretin).

A cosmetic composition comprising resveratrol may provide an increase in $UVA_{PPD}$ PF of at least 40% relative to an otherwise identical cosmetic composition without resveratrol. In some instances, a cosmetic composition comprising resveratrol may provide an increase in $UVA_{PPD}$ PF of at least 45 or 50% relative to an otherwise identical cosmetic composition without resveratrol. A maximum percent increase in $UVA_{PPD}$ PF when the cosmetic composition includes resveratrol may be 50, 55, 60, or 65% (e.g., the percent increase by be from at least 40 to 65%, relative to an otherwise identical cosmetic composition without resveratrol).

A cosmetic composition comprising ferulic acid may provide an increase in $UVA_{PPD}$ PF of at least 30% relative to an otherwise identical cosmetic composition without ferulic acid. In some instances, a cosmetic composition comprising ferulic acid may provide an increase in $UVA_{PPD}$ PF of at least 32, 35, or 37% relative to an otherwise identical cosmetic composition without ferulic acid. A maximum percent increase in $UVA_{PPD}$ PF when the cosmetic composition includes resveratrol may be 37, 40, or 45% (e.g., the percent increase by be from at least 30 to 45%, relative to an otherwise identical cosmetic composition without ferulic acid).

The total amount of antioxidant(s) that boost UVA photo-protection in the cosmetic compositions can vary but is typically about 0.01 to about 10 wt. %, based on the total weight of the cosmetic composition. Similarly, the total amount of antioxidant(s) can be about 0.01 to about 5 wt. %, about 0.01 to about 4 wt. %, about 0.01 to about 3 wt. %, about 0.01 to about 2 wt. %, about 0.1 to about 10 wt. %, about 0.1 to about 5 wt. %, about 0.1 to about 4 wt. %, about 0.1 to about 3 wt. %, about 0.1 to about 2 wt. %, or about 0.1 o about 1 wt. %, based on the total weight of the cosmetic composition.

The $UVA_{PPD}$ PF of the cosmetic composition is typically at least 4. Skin properly treated with a cosmetic composition having a $UVA_{PPD}$ PF of 4 means that it takes about 4 times longer for the skin to darken (i.e., to reach a threshold level of pigment darkening) compared to skin without treatment with the cosmetic composition. In some cases, the $UVA_{PPD}$ PF of the cosmetic composition is at least 5, 6, 7, 8, 9, 10, 11, 12, 13, 14, 15, 16, 17, 18, 19, 20, or higher. The cosmetic composition may have a maximum $UVA_{PPD}$ PF 20, 25, or 30. Based on the $UVA_{PPD}$ PF, the cosmetic compositions can be characterized based on their "PA" value, another common system used to characterize the degree of UVA protection provided by a sunscreen. The term "PA" designates "Protection Grade of UVA" and this characterization method, which was originally developed in Japan, is widely used worldwide. It is based on PPD (Persistent Pigment Darkening) at 2-4 hours of UVA exposure. The term "PA" is followed by one or more "+" symbols (plus signs). More plus signs represent greater protection from UVA rays.

A cosmetic composition designated as "PA+" means that the cosmetic composition has a $UV_{PPD}$ PF of from 2 to 4;

A cosmetic composition designated as "PA++" means that the cosmetic composition has a $UV_{PPD}$ PF of from above 4 to 8;

A cosmetic composition designated as "PA+++" means that the cosmetic composition has a $UV_{PPD}$ PF of from above 8 to 16; and A cosmetic composition designated as "PA++++" means that the cosmetic composition has a $UV_{PPD}$ PF of greater than 16.

The cosmetic compositions of the present disclosure can have a Protection Grade of UVA (PA) of PA+, of PA++, of PA+++, or of PA++++.

The cosmetic compositions of the present disclosure provide broad spectrum photo-protection to skin and therefore provide protection from both UVA and UVB radiation. Sun Protection Factor (SPF) is a measure of UVB protection. Typically, the cosmetic compositions of the present disclosure have an SPF of at least 5. The SPF however, can vary as needed. The type and amount of UVB filters can be varied to obtain a desired level of SPF. In some instances, the SPF of the cosmetic composition is at least 10, 20, 25, 30, 35, 40, 45, 50, 55, 60, 65, 70, 75, 80, 85, 90, 95, 100, 125, 150, 175, or 200. The maximum SPF of the cosmetic composition may be 100, 125, 150, 175, 200, 250, or 300. Accordingly, the cosmetic compositions of the present disclosure can have an SPF of about 5 to about 250, about 50 to about 200, about 5 to about 150, about 5 to about 125, about 5 to about 100, about 5 to about 75, about 10 to about 250, about 10 to about 200, about 10 to about 150, about 10 to about 125, about 10 to about 100, about 15 to about 250, about 15 to about 200, about 15 to about 150, about 15 to about 125, or about 15 to about 100. In some cases, the SPF of the cosmetic composition is about 5 to about 150, about 10 to about 125, about 15 to about 100, or about 30 to about 75.

The ratio of $UVA_{PPD}$ PF to SPF ($UVA_{PPD}$ PF:SPF) can vary but in some instances is about 1:1 to about 1:20. For instance, for a ratio of about 1:1, if the $UVA_{PPD}$PF of the sunscreen composition is about 10, the SPF would also be about 10. For a ratio of about 1:20, if the $UVA_{PPD}$ PF of the sunscreen composition is about 10, the SPF would be about 200. The ratio of $UVA_{PPD}$ PF to SPF ($UVA_{PPD}$ PF:SPF) may also be about 1:1 to about 1:15, about 1:1 to about 1:12; about 1:1 to about 1:10, about 1:1 to about 1:8, or about 1:1 to about 1:5.

The cosmetic compositions of the present disclosure include at least one antioxidant that boosts photo-protection from UVA radiation. Therefore, these antioxidants can be combined with UVA filters, for example organic UVA filters, to boost (increase) the UVA photo-protection provided by the UVA filters. UVA filters are categorized as either UVA1 or UVA 2 filters depending on the range of UVA radiation for which they provide protection. UVA1 filters cover a range of 340 nm to 400 nm. UVA2 filters cover a range of 320 nm to 340 nm. The only organic UVA1 filter approved for use in the United States by the US Food and Drug Administration (FDA) is avobenzone. Organic filters that provide protection from UVA2 radiation include dioxybenzone, oxybenzone, sulisobenzone, ecamsule, and meradimate, but these filters also provide protection from UVB radiation. One or more UVA1 and/or UVA2 filters may optionally be included in the cosmetic compositions.

The total amount of UVA filters (both UVA1 and UVA2) in the cosmetic compositions may vary but is typically from none (zero) to about 20 wt. %, based on the total weight of the cosmetic composition. If UVA filter(s) are present in the cosmetic composition, the total amount of UVA filters may be in an amount greater than zero to about 20 wt. %, based on the total weight of the cosmetic composition. In some cases, the total amount of UVA filters in the cosmetic compositions is from about 0.01 to about 20 wt. %, about 0.01 to about 15 wt. %, about 0.01 to about 10 wt. %, about 0.01 to about 8 wt. %, about 0.01 to about 6 wt. %, about 0.01 to about 5 wt. %, about 0.1 to about 20 wt. %, about 0.1 to about 15 wt. %, about 0.1 to about 10 wt. %, about 0.1 to about 8 wt. %, about 0.1 to about 6 wt. %, about 0.1 to about 5 wt. %, about 1 to about 20 wt. %, about 1 to about 15 wt. %, about 1 to about 10 wt. %, about 1 to about 8 wt. %, about 1 to about 6 wt. %, or about 1 to about 5 wt. %, based on the total weight of the cosmetic composition.

The cosmetic compositions include at least one organic UVB filter. In some instances it is preferable to include more than one organic UVB filter, for example, at least 2, 3, 4, or 5 UVB filters. Non-limiting examples of UVB filters include a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and mixtures thereof.

In some instances, at least one UVB filter may be selected from the group consisting of methylene bis-benzotriazolyl tetramethylphenol (Tinosorb M), diethylamino hydroxybenzoyl hexyl benzoate, ethylhexyl salicylate, ethylhexyl methoxycinnamate, isoamyl methoxycinnamate, polysilicone-15, menthyl anthranilate, ethylhexyl dimethyl PABA, aminobenzoic acid (PABA), cinoxate, dioxybenzone, ecamsule (Mexoryl SX), ensulizole (phenylbenzimiazole sulfonic acid), homosalate, meradimate (menthyl anhranilate), octocrylene, octinoxate (octyl methoxycinnamate), octisalate (octyl salicylate), oxybenzone, padimate 0, sulisobenzone, trolamine salicylate, and a mixture thereof.

The cosmetic compositions of the present disclosure may optionally include one or more inorganic UV filters that provide protection from UVA and/or UVB radiation. In some instances, however, the cosmetic compositions of the present disclosure are free or essentially free of inorganic UVA and/or inorganic UVB filters.

A more exhaustive but non-limiting list of UV filters that may be included in the cosmetic compositions is provided later, under the heading "UV Filters."

The total amount of UVB filters in the cosmetic compositions of the present disclosure can vary and will depend on the desired SPF for the cosmetic composition. Higher amounts of UVB filters typically provide higher SPFs. In some instances, the total amount of UVB filters in the sunscreen compositions may be about 0.1 to about 40 wt. %, based on the total weight of the cosmetic composition. The total amount of UVB filters may be about 0.1 to about 35 wt. %, about 0.1 to about 30 wt. %, about 0.1 to about 25 wt. %, about 0.1 to about 20 wt. %, about 0.1 to about 15 wt. %, about 0.1 to about 10 wt. %, about 1 to about 40 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, about 5 to about 40 wt. %, about 5 to about 35 wt. %, about 5 to about 30 wt. %, about 5 to about 25 wt. %, about 5 to about 20 wt. %, about 5 to about 15 wt. %, or about 5 to about 10 wt. %, based on the total weight of the cosmetic composition.

The inventors discovered that antioxidants that boost photo-protection from UVA radiation synergistically interact with organic UV filters to significantly increase the UVA protection provided by a cosmetic composition comprising the antioxidant(s) and the organic UV filter(s). This allows for lower amounts of UVA filters to be used while obtaining the same or higher degree of protection from UVA radiation, and therefore changes the ratio of the total amount of organic UVA filter(s) to the total amount of UVB filter(s) (UVA Filters:UVB Filters) needed in a cosmetic composition for attaining broad spectrum photo-protection. In some instances the ratio of the total amount of UVA filters to the total amount of UVB filters is about 1:1 to about 1:20. In some cases, the ratio of the total amount of UVA filters to the total amount of UVB filters is about 1:1 to about 1:15, about 1:1 to about 1:10, about 1:1 to about 1:8, about 1:2 to about 1:20, about 1:2 to about 1:15, about 1:2 to about 1:10, about 1:2 to about 1:8, about 1:3 to about 1:20, about 1:3 to about 1:15, about 1:3 to about 1:10, about 1:3 to about 1:8.

In some instances, the cosmetic compositions of the present disclosure may include avobenzone, a UVA1 filter. When the cosmetic compositions include avobenzone, the total amount of avobenzone to the total amount of UVB filters in the cosmetic composition may be about 1:1 to about 1:20. In some cases, the ratio of avobenzone to the total amount of UVB filters is about 1:1 to about 1:15, about 1:1 to about 1:10, about 1:1 to about 1:8, about 1:2 to about 1:20, about 1:2 to about 1:15, about 1:2 to about 1:10, about 1:2 to about 1:8, about 1:3 to about 1:20, about 1:3 to about 1:15, about 1:3 to about 1:10, about 1:3 to about 1:8.

The antioxidant(s) that boost photo-protection from UVA radiation and the UV filters are combined in a cosmetically acceptable carrier to form the cosmetic compositions of the present disclosure.

The cosmetically acceptable carrier allows the antioxidant(s) and UVB filter(s) to be combined and applied to skin in a form that is appropriate for application to skin, in particular, human skin. Perhaps the most common cosmetically acceptable carrier is water, and in some instances, the cosmetically acceptable carrier for the cosmetic compositions of the present disclosure is water (but is not required to be water). Non-limiting examples of cosmetically acceptable carriers other than water include glycerin, $C_{1-4}$ alcohols, organic solvents, fatty alcohols, fatty ethers, fatty esters, polyols, glycols, vegetable oils, mineral oils, liposomes, laminar lipid materials, water, or a mixture thereof. Non-limiting examples of organic solvents include mono-alcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds. In some cases the cosmetic compositions of the present disclosure include, as a cosmetically acceptable carrier, at least water.

The total amount of cosmetically acceptable carrier in the cosmetic compositions can vary but is typically about 40 to about 90 wt. %, based on the total weight of the cosmetic composition. In some cases, the total amount of cosmetically acceptable carrier is about 40 to about 85 wt. %, about 40 to about 80 wt. %, about 45 to about 90 wt. %, about 45 to about 85 wt. %, about 45 to about 80 wt. %, about 50 to about 90 wt. %, about 50 to about 85 wt. %, or about 50 to about 80 wt. %, based on the total weight of the cosmetic composition.

In some cases, the cosmetic compositions of the present disclosure include at least water as a cosmetically acceptable carrier. The total amount of water in the cosmetic composition can vary but is typically about 35 to about 95 wt. %, based on the total weight of the cosmetic composition. In some cases, the total amount of water is about 35 to about 90 wt. %, about 35 to about 85 wt. %, about 35 to about 80 wt. %, about 40 to about 85 wt. %, about 40 to about 80 wt. %, about 45 to about 90 wt. %, about 45 to about 85 wt. %, about 45 to about 80 wt. %, about 50 to about 90 wt. %, about 50 to about 85 wt. %, about 50 to about 80 wt. %, about 60 to about 90 wt. %, about 60 to about 85 wt. %, or about 60 to about 80 wt. %, based on the total weight of the cosmetic composition.

The cosmetic compositions of the present disclosure may include at least one water-soluble solvent. The term "water-soluble solvent" is interchangeable with the term "water-miscible solvent" and means a compound that at 25° C. and at atmospheric pressure (760 mmHg) has a solubility of at least 70% in water. In some cases, the water-soluble solvent has a solubility of at least 80%, 90%, or 95% in water at 25° C. and at atmospheric pressure (760 mmHg). Non-limiting examples of water-soluble solvents include, for example, glycerin, alcohols (for example, $C_1$-8 or $C_1$-4 alcohols), organic solvents, polyols, glycols, and a mixture thereof.

Non-limiting examples of organic solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof.

The total amount water-soluble solvent(s) in the cosmetic composition may vary but is typically about 0.1 to about 50 wt. %, based on the total weight of the cosmetic composition. In some instances, the total amount of the one or more water-soluble solvents may be about 0.1 to about 40 wt. %, about 0.1 to about 30 wt. %, about 0.1 to about 20 wt. %, about 0.1 to about 10 wt. %, about 0.1 to about 5 wt. %, about 1 to about 50 wt. %, about 1 to about 40 wt. %, about 1 to about 30 wt. %, about 1 to about 20 wt. %, about 1 to about 15 wt. %, about 1 to about 10 wt. %, or about 1 to about 5 wt. %, based on the total weight of the cosmetic composition.

Solubilizing agents are compounds that help solubilize the antioxidant(s) and/or the UV filters in the cosmetic compositions. A particularly useful but non-limiting example of a solubilizing agent is a hydrotrope. Hydrotropes (or hydrotropic agents) are a diverse class of typically water-soluble compounds that may be characterized by an amphiphilic molecular structure and an ability to dramatically increase the solubility of poorly soluble organic molecules in water. Many hydrotropes have an aromatic structure with an ionic moiety, while some of them are linear alkyl chains. Although hydrotropes can resemble surfactants and have the ability to reduce surface tension, their small hydrophobic units and relatively shorter alkyl chains distinguish them as a separate class of amphiphiles. Consequently their hydrophobicity is not sufficient enough to create well organized self-associated structures, such as micelles, even with a high concentration.

Non-limiting examples of hydrotopes include sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Additional examples of hydrotopes that may be used can be found in Lee J. et al., "*Hydrotropic Solubilization of Paclitaxel: Analysis of Chemical Structures for Hydrotropic Property*", PHARMACEUTICAL RESEARCH, Vol. 20, No. 7, 2003; and Lee S. et al., "*Hydrotropic Polymers: Synthesis and Characterization of Polymers Containing Picolylnicotinamide Moieties*", MACROMOLECULES, 36, 2248-2255, 2003, which are incorporated herein by reference in their entirety. In some cases, particularly useful hydrotropes include nicotinamide (niacinamide), caffeine, sodium PCA, sodium salicylate, urea, and dihydroxyethyl urea, in particular, nicotinamide (niacinamide) and/or caffeine. A combination of two or more, three or more, or four or more hydrotopes may also be used in the cosmetic compositions.

The total amount of solubilizing agent(s) in the cosmetic compositions of the present disclosure, if present, may vary but are typically in an amount of about 0.01 to about 20 wt. %, based on the total weight of the cosmetic composition. The total amount of solubilizing agent(s) may be in an amount of about 0.01 to about 15 wt. %, about 0.01 to about 10 wt. %, about 0.01 to about 8 wt. %, about 0.1 to about 20 wt. %, about 0.1 to about 15 wt. %, about 0.1 to about 10 wt. %, about 0.1 to about 8 wt. %, about 0.5 to about 20 wt. %, about 0.5 to about 15 wt. %, about 0.5 to about 10 wt. %, about 0.5 to about 8 wt. %, about 1 to about 20 wt. %, about 1 to about 15 wt. %, about 1 to about 10 wt. %, or about 1 to about 8 wt. %, based on the total weight of the cosmetic composition.

The cosmetic compositions of the present disclosure may include at least one emulsifier. Many emulsifiers are known in the art and may be used, including, amphoteric, anionic, cationic, and nonionic emulsifiers. In some instances, it is useful to include at least one nonionic emulsifier. Non-limiting examples of nonionic emulsifiers include polyol esters, a glycerol ethers, oxyethylenated and/or oxypropylenated ethers, ethylene glycol polymers, and mixtures thereof. For example, in some cases the emulsifier includes a mixture of a polyol ester and an ethylene glycol polymer, for example, a mixture of glyceryl stearate and PEG-100 stearate. In some instances, an oxyalkylenated organosiloxane emulsifier is included. Non-limiting examples include dimethicone/PEG-10/15 crosspolymer, PEG-15 lauryl dimethicone crosspolymer, PEG-15 lauryl dimethicone crosspolymer, PEG-10 lauryl dimethicone crosspolymer, or a mixture thereof. In some instances, the cosmetic compositions of the present disclosure are in the form of an emulsion. For example, a water in oil emulsion, an oil in water emulsion, or a silicone in water emulsion.

A more exhaustive but non-limiting list of emulsifiers that may be included in the cosmetic compositions is provided later, under the heading "Emulsifiers."

The total amount of emulsifier(s) in the cosmetic compositions, when present, may vary but is typically about 0.01 to about 10 wt. %, based on the total weight of the composition. In some instances, the total amount of the one or more emulsifiers in the cosmetic compositions is about 0.1 to about 10 wt. %, about 0.1 to about 8 wt. %, about 0.1 to about 5 wt. %, about 0.5 to about 10 wt. %, about 0.5 to about 8 wt. %, about 0.5 to about 5 wt. %, about 1 to about 10 wt. %, about 1 to about 8 wt. %, or about 1 to about 5 wt. %, based on the total weight of the cosmetic composition.

The cosmetic compositions of the present disclosure may include at least one silicone compound (which may also be referred to as silicone oils). Non-limiting examples of silicone compounds include polydimethylsiloxanes, polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and mixtures thereof. More specific but non-limiting examples of silicone compounds include dimethicone, cyclomethicone, polysilicone-11, phenyl trimethicone, trimethylsilylamodimethicone, and stearoxytrimethylsilane. In some cases, the cosmetic composition includes dimethicone, and optionally one or more additional silicone compounds.

Other examples of silicone compounds that may be mentioned include volatile linear or cyclic silicone oils, especially those with a viscosity 8 centistokes ($8 \times 10^6$ m$^2$/s) and especially containing from 2 to 7 silicon atoms, these silicones optionally comprising alkyl or alkoxy groups containing from 1 to 10 carbon atoms. As volatile silicone oils that may be used in the disclosure, mention may be made especially of octamethylcyclotetrasiloxane, decamethylcyclopentasiloxane, dodecamethyl-cyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

A more exhaustive but non-limiting list of silicone compounds that may be included in the cosmetic compositions is provided later, under the heading "Silicone Compounds."

The total amount of silicone compound(s) in the cosmetic compositions can vary but is typically about 0.1 to about 20 wt. %, based on the total weight of the cosmetic composition. In some cases, the total amount of silicone compound(s) is about 0.1 to about 15 wt. %, about 0.1 to about 12 wt. %, about 0.1 to about 10 wt. %, about 0.1 to about 8 wt. %, about 0.1 to about 5 wt. %, about 0.5 to about 20 wt. %, about 0.5 to about 15 wt. %, about 0.5 to about 10 wt. %, about 0.5 to about 8 wt. %, about 0.5 to about 5 wt. %, about 1 to about 20 wt. %, about 1 to about 15 wt. %, about 1 to about 10 wt. %, about 1 to about 8 wt. %, or about 1 to about 5 wt. %, based on the total weight of the cosmetic composition.

At least one fatty compound may be included in the cosmetic compositions of the present disclosure. Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. In some instances, the at least one fatty compound includes one or more fatty alcohols, fatty acids, esters of fatty acids and fatty alcohols (for example, cetyl palmitate, cetyl stearate, myristyl myristate, myristyl stearate, cetyl myristate, and stearyl stearate).

A more exhaustive but non-limiting list of fatty compounds that may be included in the cosmetic compositions is provided later, under the heading "Fatty Compounds."

The total amount of fatty compound(s) in the cosmetic compositions can vary but is typically about 0.1 to about 30 wt. %, based on the total weight of the cosmetic composition. In some cases, the total amount of fatty compound(s) is about 0.1 to about 25 wt. %, about 0.1 to about 20 wt. %, 0.1 to about 15 wt. %, about 0.1 to about 12 wt. %, about 0.1 to about 10 wt. %, about 0.1 to about 8 wt. %, about 0.1 to about 5 wt. %, about 0.5 to about 30 wt. %, about 0.5 to about 25 wt. %, about 0.5 to about 20 wt. %, about 0.5 to about 15 wt. %, about 0.5 to about 10 wt. %, about 0.5 to about 8 wt. %, about 0.5 to about 5 wt. %, about 1 to about 30 wt. %, about 1 to about 25 wt. %, about 1 to about 20 wt. %, about 1 to about 15 wt. %, about 1 to about 10 wt. %, about 1 to about 8 wt. %, or about 1 to about 5 wt. %, based on the total weight of the cosmetic composition.

The cosmetic compositions of the instant disclosure may include at least one thickening agent. The term "thickening agent" is interchangeable with the terms "thickener," "gelling agent," and "viscosity modifier." Non-limiting examples of useful thickening agents include cellulose polymers, gums, modified or unmodified carboxyvinyl polymers, polyacrylamides, copolymers of acrylic acid and of acrylamide, sodium salts of polyhydroxycarboxylic acids, optionally crosslinked and/or neutralized 2-acrylamido-2-methylpropanesulphonic acid polymers and copolymers, polyacrylic acid/alkyl acrylate, glucans, modified or unmodified starches, silicas, and mixtures thereof.

In some instances, the at least one thickening agent comprises a gum, especially those derived from natural sources. Non-limiting examples of useful gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosacharide gum, and mixtures thereof. Particularly preferred gums include xanthan gum, guar gum, biosaccharide gum, cellulose, acacia gum, seneca gum, sclerotium gum, agarose, gellan gum, and mixtures thereof. A more exhaustive list of useful thickening agents that may be included is provided later, under the heading "Thickening Agent."

The total amount of thickening agent(s) in the cosmetic compositions may vary but is typically about 0.01 to about 10 wt. %, based on the total weight of the cosmetic composition. The total amount of the at least one thickening agent may be about 0.01 to about 6 wt. %, about 0.01 to about 5 wt. %, about 0.01 to about 3 wt. %, about 0.01 to about 1 wt. %, about 0.1 to about 10 wt. %, about 0.1 to about 6 wt. %, about 0.1 to about 5 wt. %, about 0.1 to about 3 wt. %, or about 0.1 to about 1 wt. %, based on the total weight of the cosmetic composition.

The cosmetic compositions of the present disclosure may optionally include at least one film-forming polymer. For instance, non-limiting examples of film-forming polymers include vinyl polymers, polyesters, polyamides, polyureas, and a mixture thereof. The one or more film-forming polymers may be polyethyleneimine, polylysine, polyvinyl alcohols, poly(hydroxyethyl (meth)acrylate), hydroxyalkylcelluloses, polyacrylic acid, polyvinylimidazoles, polypropyleneimines, polyallylamines, chitosan, carboxyalkylcelluloses, aminoalkylcelluloses, maleic, fumaric and/or itaconic acid or anhydride polymers, polyamidoamines, and a mixture thereof.

The one or more film-forming polymers may be copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl(meth)acrylate and/or isobutyl (meth)acrylate/ $C_1$-$C_4$ alkyl(meth)acrylate copolymers; (meth)acrylic acid/ ethyl acrylate/methyl methacrylate terpolymers and tetrapolymers; methyl methacrylate/butyl or ethyl acrylate/ hydroxyethyl or 2-hydroxypropyl acrylate or methacrylate/ (meth)acrylic acid tetrapolymers; copolymers of acrylic acid and of $C_1$-$C_4$ alkyl methacrylate; terpolymers of vinylpyrrolidone, of acrylic acid and of $C_{1-20}$ alkyl methacrylate; amphoteric copolymers; vinyl esters of branched acids; vinyl esters of benzoic acid; copolymers of (meth)acrylic acid and of at least one olefinic monomer; copolymers of vinyl monoacid and/or of allylic monoacid; and a mixture thereof. In some cases, the one or more film-forming polymers include VP/dimethylaminoethylmethacrylate copolymer.

The total amount of the one or more film-forming polymers (other than the one or more latex polymers) may vary but is typically about 0.01 to about 10 wt. %, based on the total weight of the hair-treatment composition. The total amount of the one or more film-forming polymers (other than the one or more latex polymers) may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, or about 0.1 to about 5 wt. %.

In some instances, the cosmetic compositions of the present disclosure include one or more skin active ingredients. For example, the skin active ingredient may be a humectant, a moisturizing ingredient, an anti-aging agent, a depigmenting agent, an anti-wrinkle agent, an agent that treats oily skin, and a mixture thereof. In some cases, the one or more skin active ingredients may be adenosine, ascorbic acid, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, or a mixture thereof.

The total amount of skin active ingredient(s) may be from about 0.001 to about 10 wt. %, based on the total weight of the composition. In some instances, the amount of skin active ingredient(s) may be from about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the amount of the skin active ingredients may be from about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the total amount of the skin active ingredients may be from 0.1 wt. % to about 9 wt. %, about 8 wt. %, about 7 wt. %, about 6 wt. %, about 5 wt. %, about 4 wt. %, about 3 wt. %, or about 2 wt. %. Finally, the amount of the skin active ingredients may be from about 0.5 wt. % to about 5 wt. %, about 0.5 wt. % to about 3 wt. %, 0.5 wt. % to about 2 wt. %, or about 1 wt. %.

The methods described in the present disclosure include topically applying the cosmetic compositions described herein to the skin and/or hair. The cosmetic compositions may be applied once or may be applied repeatedly over a period of time to ensure that the skin consistently enjoys broad spectrum photoprotection over a period of time. In some instances, the cosmetic compositions of the present disclosure are sunscreen compositions, i.e., the compositions are formulated and used specifically for preventing damage to the skin and/or hair by the sun. The cosmetic compositions may be in a variety of different forms. For example, the cosmetic compositions may be a spray, a lotion, a gel, a cream, a stick (or bar), or a foam. In some cases, it is desirable, especially for sunscreen composition, for the cosmetic compositions of the present disclosure to be in spray form, for example, a pump spray or an aerosol spray.

The cosmetic compositions may be clear or transparent. The term "transparent" or "clear" means that the composition/product allows light to pass through so that objects behind can be seen. A transparent material allows light to pass through, and makes it possible to distinguish alphanumeric characters using 5 mm thick samples. A simple example of a transparent material is a glass window. One can see through a glass window. More specifically, term "transparent" relates to a material having a maximum light transmittance value, at a wavelength equal to 500 nm, through a sample 1 cm thick, of at least 60% and preferably of at least 70%.

In some instance, the cosmetic compositions of the instant disclosure may be opaque or cloudy. The term "opaque" or "cloudy" means that the composition/product that is not transparent. Steam on a window is an example of an opaque or cloudy scenario.

Finally, the instant disclosure relates to methods of using the compositions described herein, for example, in the treatment of skin (in addition to providing broad spectrum photo protection to the skin). For example, the compositions may be used in methods for: providing anti-aging benefits to the skin; whitening or preventing darkening of skin; improving the appearance of skin; strengthening skin's natural antioxidant defenses; diminishing the visible signs of skin aging; and improving skin's radiance and firmness. These methods typically entail applying the compositions described herein to the skin.

More exhaustive but non-limiting lists of components useful in the instant compositions disclosed herein are presented below.

UV Filters

UV filters are well known in the art for their use in stopping UV radiation. For example, the UV filter may be one or more organic UV filters and/or one or more inorganic UV filters. Non-limiting examples of UV filters include:
  i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.
  ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);
  iii. Inorganic UV filters such as titanium oxide and zinc oxide, iron oxide, zirconium oxide and cerium oxide; and
  iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl saliciate, octocrylene, polysilicone-15, butyl methoxydibenzoylmethane, menthyl anthranilate, and ethylhexyl dimethyl PABA.

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

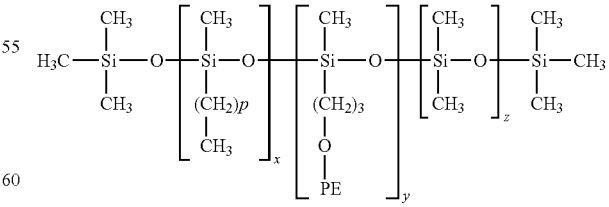

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

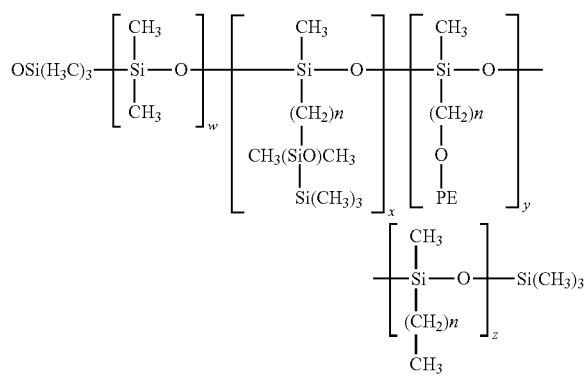

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially cross-linked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Fatty Compounds

The hair conditioning compositions may also include at least one fatty compound. A "fatty compound" is an organic compound that is not soluble in water at normal temperature (25° C.) and at atmospheric pressure (750 mmHg) (solubility below 10%). In some instances, the solubility in water may be below 5%, below 1%, or below 0.1%. Moreover, fatty compounds are generally soluble in one or more organic solvents under the same conditions of temperature and pressure, for example organic solvents such as chloroform, ethanol, benzene or decamethylcyclopentasiloxane.

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. In some instances, the at least one fatty compound includes one or more fatty alcohols, fatty acids, esters of fatty acids, and/or esters of fatty alcohols (for example, cetyl palmitate, cetyl stearate, myristyl myristate, myristyl stearate, cetyl myristate, and stearyl stearate (a mixture of which is referred to as "cetyl esters")).

Fatty compounds include hydrocarbons, fatty alcohols, fatty alcohol derivatives, fatty acids, fatty acid derivatives, fatty esters, fatty ethers, oils, waxes, etc. The fatty compounds may be liquid or solid at room temperature and at atmospheric pressure (25° C., 1 atm). Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Non-limiting examples of hydrocarbons include linear or branched, optionally cyclic $C_6$-$C_{16}$ alkanes; hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

The fatty alcohols that can be used may be liquid at 25° C., 1 atm, or may even be solid. They may even be glycerolated and/or oxyalkylenated, and may include from 8 to 30 carbon atoms. They may be saturated or unsaturated. The fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, isotridecyl alcohol, and a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, and 2-hexyldecanol.

The unsaturated liquid fatty alcohols include in their structure at least one double or triple bond and preferably one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol and undecylenyl alcohol can be cited.

Non-limiting examples of solid fatty alcohols include linear or branched, saturated or unsaturated alcohols containing from 8 to 30 carbon atoms, for example, myristic alcohol, cetyl alcohol, stearyl alcohol and their mixture, cetylstearyl alcohol.

Non-limiting examples of liquid fatty esters include esters from a $C_6$-$C_{32}$ fatty acid and/or a $C_6$-$C_{32}$ fatty alcohol, and are liquid at 25° C., 1 atm. These esters may be liquid esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some cases, it is particularly useful to include cetyl esters in the hair conditioning compositions. Cetyl Esters is a mixture of the following esters of saturated fatty acids and fatty alcohols: cetyl palmitate, cetyl stearate, myristyl myristate, myristyl stearate, cetyl myristate, and stearyl stearate.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used.

Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Mention may also be made of sugar esters and diesters of $C_6$-$C_{30}$ and preferably $C_{12}$-$C_{22}$ fatty acids. The term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides. Examples of suitable sugars that may be mentioned include saccharose, glucose, galactose, ribose, fucose, maltose, fructose, mannose, arabinose, xylose and lactose, and derivatives thereof, especially alkyl derivatives, such as methyl derivatives, for instance methylglucose. The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds. The esters according to this variant may also be chosen from mono-, di-, tri- and tetraesters, and polyesters, and mixtures thereof. These esters may be, for example, oleates, laurates, palmitates, myristates, behenates, cocoates, stearates, linoleates, linolenates, caprates and arachidonates, and mixtures thereof, such as, in particular, oleopalmitate, oleostearate or palmitostearate mixed esters. More particularly, use is made of monoesters and diesters and in particular of sucrose, glucose or methylglucose mono- or dioleates, stearates, behenates, oleopalmitates, linoleates, linolenates or oleostearates.

As oils of plant origin or synthetic triglycerides that may be used in the composition of the invention as liquid fatty esters, the following can be cited, for example, triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, caprylic/capric acid triglycerides, jojoba oil, and shea butter oil.

The solid fatty acid esters and/or fatty alcohol esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

The liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Non-limiting examples of waxes include carnauba wax, candelilla wax, esparto wax, paraffin wax, ozokerite, plant waxes such as olive tree wax, rice wax, hydrogenated jojoba wax or absolute flower waxes, such as the blackcurrant blossom essential wax sold by Bertin (France), or animal waxes such as beeswaxes or modified beeswaxes (cerabellina), and ceramides. Non-limiting examples of ceramides include N-linoleyldihydrosphingosine, N-oleyldihydrosphingosine, N-palmityldihydrosphingosine, N-stearyldihydrosphingosine or N-behenyldihydrosphingosine, or mixtures of these compounds.

Non-limiting olyglycerol esters of fatty acids include those of the following formula:

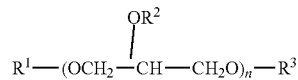

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_6$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Non-limiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Implementation of the present disclosure is provided by way of the following examples. The examples serve to illustrate the technology without being limiting in nature.

EXAMPLES

Example 1

Sunscreen Formulations of SPF 30

| | | A | B | C | D | E | F |
|---|---|---|---|---|---|---|---|
| | INCI US | | | | | | |
| Antioxidants | PHLORETIN | — | — | — | — | — | 0.5 |
| | POLYDATIN | — | — | 0.5 | — | — | — |
| | FERULIC ACID | — | — | — | 0.5 | — | — |
| | RESVERATROL | — | — | — | — | 0.5 | — |
| | BAICALIN | — | 0.5 | — | — | — | — |
| UVA Filter | AVOBENZONE | 3 | 3 | 3 | 3 | 3 | 3 |
| UVB Filter | HOMOSALATE | 5 | 5 | 5 | 5 | 5 | 5 |
| | ETHYLHEXYL SALICYLATE | 5 | 5 | 5 | 5 | 5 | 5 |
| | OCTOCRYLENE | 7 | 7 | 7 | 7 | 7 | 7 |
| Fatty Compound | DICAPRYLYL CARBONATE, CETYL ALCOHOL, MYRISTIC ACID, PALMITIC ACID, AND/OR STEARIC ACID | 3.6 | 3.6 | 3.6 | 3.6 | 3.6 | 3.6 |
| Nonionic Emulsifier | PEG-100 STEARATE AND/OR GLYCERYL STEARATE | 3 | 3 | 3 | 3 | 3 | 3 |
| Solubilizing Agent | CAFFEINE AND/OR NIACINAMIDE | 5 | 5 | 5 | 5 | 5 | 5 |
| Silicone Compound | DIMETHICONE AND/OR DIMETHICONE/VINYL DIMETHICONE CROSSPOLYMER | 3 | 3 | 3 | 3 | 3 | 3 |
| Filler | SILICA | 3 | 3 | 3 | 3 | 3 | 3 |
| Water Soluble Solvent | CAPRYLYL GLYCOL AND/OR GLYCERIN | 3.3 | 3.3 | 3.3 | 3.3 | 3.3 | 3.3 |
| Thickening Agent | AMMONIUM POLYACRYLOYLDIMETHYL TAURATE AND/OR XANTHAN GUM | 0.9 | 0.9 | 0.9 | 0.9 | 0.9 | 0.9 |
| Miscellaneous | Preservative(s), chelating agent(s), Vitamin(s), etc. | ≤3 | ≤3 | ≤3 | ≤3 | ≤3 | ≤3 |
| Water | WATER | QS | QS | QS | QS | QS | QS |

Example 2

In Vivo PPD

Sunscreen formulation A (of Example 1), which does not include any antioxidants, was compared with sunscreen formulations B and C, which include 0.5 wt. % of the antioxidants baicalin and polydatin, respectively. The degree of UVA protection provided by each of the formulations was determined in terms of $UV_{PPD}$ PF. Based on these results, the formulations were assigned a "PA" value, which represents the protection grade of UVA. PA values are commonly used to simplify the results of $UV_{PPD}$PF testing. It ranges from PA+ to PA++++, wherein:

PA+ is sunscreen with a $UV_{PPD}$ PF from 2 to 4;
PA++ is a sunscreen with $UV_{PPD}$ PF from above 4 to 8;

PA+++ is a sunscreen with a $UV_{PPD}$ PF from above 8 to 16; and

PA++++ is a sunscreen with a $UV_{PPD}$ PF of greater than 16.

The $UV_{PPD}$ PF for each of sunscreen formulations A, B, and C was determined according to ISO 24442, which was adopted by the Japan Cosmetic Industry Association in 2012 for characterization of UVA protection and is incorporated herein by reference in its entirety. The area of the back between the scapula line and the waste is utilized for testing using a light Source such as a 150 watt Xenon Arc Solar Simulator equipped with an Ultraviolet (UV) reflecting dichroic mirror, 3 mm thick Schott WG-335 filter together with a 1 mm thick Schott UG-11 filter to produce simulation of the UVA solar spectrum. UVA radiation can be monitored continuously during exposure using a Model DCS-1 Sunburn UV Meter/Dose Controller System (Solar Light Co.), formerly known as the Robertson-Berger Sunburn meter (R-B meter). The threshold dose for PPD in unprotected skin is determined over the mid to lowed back by administering series of exposures in 25% dose increments of UVA radiation in geometric progression. The minimum PPD dose (MPPD) is the smallest UVA dose required to persist for more than 2 hours after exposure. A minimum of 5 exposures are made. The MPPD of unprotected skin is determined under standardized lighting conditions 2 to 4 hours after exposures. Persistent pigmentation on each sub site is graded and the mean UVA Protection Factor ($UVA_{ppd}$ PF) of the sample, when at least 5 subjects tested is reported.

The testing results are summarized below and graphically presented in FIG. 1.

| Sunscreen Formulation | $UV_{PPD}$ PF | PA Value |
|---|---|---|
| Formulation A (no antioxidants) | 8 | PA++ |
| Formulation B (0.5 wt. % baicalin) | 8.8 | PA+++ |
| Formulation C (0.5 wt. % polydatin) | 17 | PA++++ |
| SPF free Formulation (0.5 wt. % polydatin) | 1.7 | — |

The data show that sunscreen formulation B, containing baicalin, exhibited a slight improvement in both $UV_{PPD}$ PF and PA Value (about 10% improvement in $UV_{PPD}$PF). Formulation C, containing polydatin, exhibited an much more pronounced improvement in $UV_{PPD}$ PF and PA Value (more than a 200% improvement in $UV_{PPD}$ PF). It was not known that certain antioxidants could boost UVA protection of sunscreens. Therefore, the significant improvement in $UV_{PPD}$ PF and PA values for polydatin was unexpected and surprising. Clearly it is not from the antioxidant itself (PPD value of 0.5% polydatin in formula without UV filters is only 1.7) but from a synergistic interaction with UV filters.

Example 3

In Vivo PPD

Figure 2:
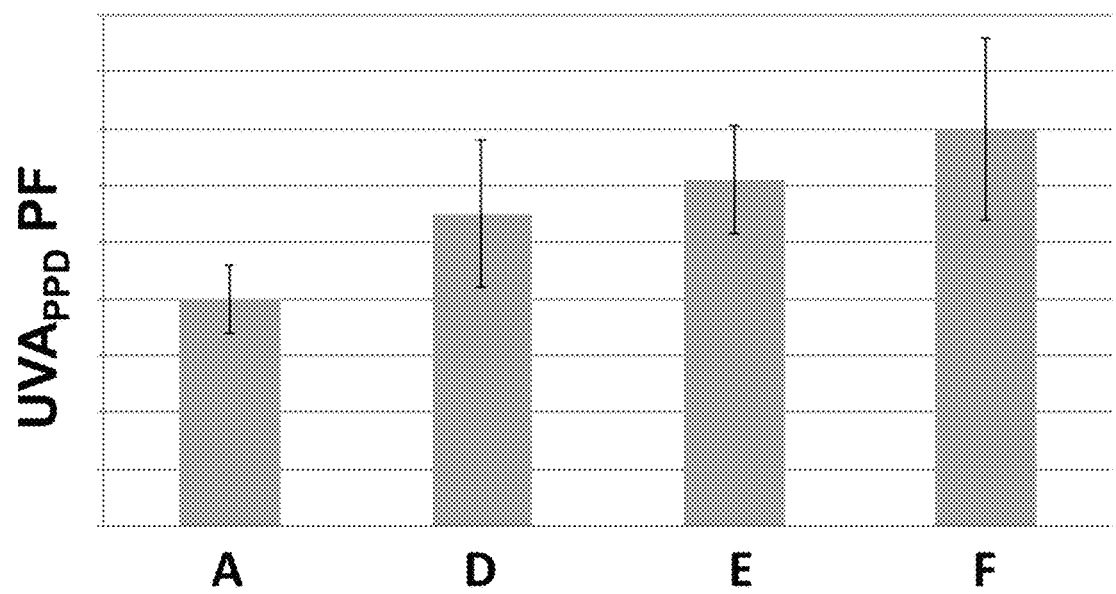
FIG. 2 is a graph showing: (A) the $UVA_{PPD}$ PF of a cosmetic composition comprising UV filters but no antioxidants that boost UVA photo-protection; (D) a cosmetic composition comprising UV filters and ferulic acid; (E) a cosmetic composition comprising UV filters and resveratrol; and (F) a cosmetic composition comprising UV filters and phloretin.

The ability of other antioxidants to boost UVA protection was investigated in the same manner described above in Example 2. Sunscreen formulation A (of Example 1), which does not include any antioxidants, was compared with sunscreen formulations D, E, and F, which include 0.5 wt. % of the antioxidants ferulic acid, resveratrol, and phloretin, respectively. The degree of UVA protection provided by each of the formulations was determined as described above in Example 2. The results are summarized below and graphically presented in FIG. 2.

| Sunscreen Formulation | $UV_{PPD}$ PF | PA Value |
|---|---|---|
| Formulation A (no antioxidants) | 8 | PA++ |
| Formulation D (0.5 wt. % ferulic acid) | 11 | PA+++ |
| Formulation E (0.5 wt. % resveratrol) | 12.2 | PA+++ |
| Formulation F (0.5 wt. % phloretin) | 14 | PA+++ |

The data show that sunscreen formulation D, containing ferulic acid, exhibited an improvement in both $UV_{PPD}$ PF and PA Value (more than 37% improvement in $UV_{PPD}$PF). Formulation E, containing resveratrol, exhibited an even greater improvement in $UV_{PPD}$ PF (more than a 52% improvement in $UV_{PPD}$ PF). Formulation F, containing phloretin, exhibited the greatest degree of improvement in $UV_{PPD}$ PF (75% improvement in $UV_{PPD}$ PF). It was not known that antioxidants could provide UVA protection. Therefore, the improvement in $UV_{PPD}$ PF and PA values for ferulic acid, resveratrol, and phloretin was unexpected and surprising. Moreover, the extent to which these antioxidants improved the $UV_{PPD}$ PF and PA value is particularly significant and surprising.

Example 4

Antioxidant Activity

In tubo antioxidant testing was carried out to determine the antioxidant profile of antioxidants that boost UVA photoprotection.

ORAC

The Oxygen Radical Absorbance Capacity (ORAC) assay is one of most commonly used methods to evaluate the capacity of antioxidants against ROS (reactive oxygen species), specific for peroxyl which is one of the most important free radicals present in the human skin environment. The ORAC assay measures the oxidative degradation of the fluorescent probe (fluorescein) after being mixed with free radical generators such as azo-initiator compounds (2,2'-Azobis(2-amidinopropane) dihydrochloride, AAPH). Azo-initiators produce the peroxyl radical by heating, which damages the fluorescent molecule, resulting in the loss of fluorescence. Antioxidants protect the fluorescent molecule from the oxidative degeneration. By quantifying the decay of fluorescence using a fluorometer, the degree of protection is determined comparing with a standard control antioxidant Trolox. The result is expressed in mol equivalent of Trolox per gram of sample (i.e., µmol TE/g). Equipment that can automatically measure and calculate the capacity is commercially available, such as the VarioSkan flash microplate reader from Thermo Scientific. To test samples for ORAC, compounds are dissolved into water-based $NaH_2PO_4$ buffer.

HORAC

The HORAC assay is another common method to examine antioxidant activity. It is specific for hydroxyl radicals. The Varioskan Flash is employed for the quantification of the capacity of an antioxidant to avert the hydroxyl radical. The hydroxyl radical, generated from hydrogen peroxide and Cobalt (II) fluoride, will quench a fluorescent probe by a hydrogen atom transfer reaction. In the presence of an antioxidant, however, the molecule will chelate the Co(II), preventing the generation of the hydroxyl radical and initially block or prevent the quenching of the probe, causing a delay in the fluorescence decay profile. The area under the fluorescence decay curves for samples with and without the presence of an antioxidant molecule are compared to that of a standard reference material and the hydroxyl radical averting capacity is determined. By quantifying the decay of fluorescence using a fluorometer, the degree of protection is determined by comparison with a standard control antioxidant Gallic Acid (standard reference material). The result is expressed in μmol equivalent of Gallic Acid per gram of sample (i.e., μmol GAE/g). Equipment that can automatically measure and calculate the capacity is commercially available, such as the VarioSkan flash microplate reader from Thermo Scientific. To test samples by using HORAC, compounds are dissolved into water-based $NaH_2PO_4$ buffer.

SORAC

The Superoxide Radical Absorbance Capacity (SORAC) assay is an in tubo method to determine the relative capacity of an antioxidant to dismutate the superoxide anion. The Varioskan Flash is employed to measure the superoxide dismutase-catalyzed dismutation of the superoxide anion in the presence of the absorbance probe, water-soluble tetrazolium salt (WST-1). WST-Formazan is produced when WST-1 is oxidized by superoxide anion that is generated by the mixture of xanthine and xanthine oxidase. One unit of SOD activity is defined as the quantity of antioxidant to obtain 50% inhibition of the rate of reduction of WST-1. The final SORAC value is expressed as one unit of SOD activity per milligram of dry weight of antioxidant material at 50% inhibition (Unit/mg).

The results for baicalin (negative example), polydatin, phloretin, resveratrol, and ferulic acid are shown below.

| Antioxidants | ORAC-peroxyl (μmol TE/g) | HORAC-hydroxyl (μmol GAE/g) | SORAC-superoxide (U/mg) |
|---|---|---|---|
| Baicalin | Medium | Weak | Medium |
| Polydatin | Strong | Strong | None |
| Phloretin | Strong | Medium | None |
| Resveartrol | Strong | Strong | None |
| Ferulic acid | Strong | Strong | Weak |
| None | No detectable value | No detectable value | No detectable value |
| Weak | <4500 | <2600 | <200 |
| Medium | 4500-10000 | 2600-10000 | 200-1000 |
| Strong | >10000 | >10000 | >1000 |

The in tubo antioxidant data above, when compared with the PPD data from Examples 2 and 3, suggests that antioxidants having strong ORAC (above mol TE/g) are effective in boosting the UVA photoprotection of cosmetic compositions. Similarly, stronger HORAC (2600-10000 μmol GAE/g) was associated with better boosting ability. The role of SORAC however, exhibited the opposite trend. The antioxidants having less SORAC (less than 200 U/mg) exhibited a boosting effect on UVA photo-protection. Baicalin, having the highest SORAC, did not boost UVA photo-protection. The fact that certain antioxidants have any boosting effect on UVA photo-protection is itself surprising and unexpected. It is further surprising and unexpected to find that the ORAC, HORAC, and SORAC of the antioxidants appears to relate to the antioxidants' boosting effect on UVA photo-protection.

The term "broad spectrum photo protection" means protection from both UVA radiation and UVB radiation.

"At least one" as used herein is synonymous with "one or more" and includes individual components as well as mixtures/combinations.

The term "treat" (and its grammatical variations) as used herein refers to the application of the cosmetic compositions of the present disclosure onto the surface of the body, and in particular the skin and/or hair of the body.

The term "volatile", as used herein, means having a flash point of less than about 100° C.

The term "non-volatile", as used herein, means having a flash point of greater than about 100° C.

The term "substituted," as used herein, means comprising one or more substituents. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "polymers," as defined herein, include homopolymers and includes copolymers formed from at least two different types of monomers.

The cosmetic methods and compositions of the present disclosure can comprise, consist of, or consist essentially of the essential elements and limitations of the disclosure described herein, as well as any additional or optional ingredients, components, or limitations described herein or otherwise useful. Additionally any component that is positively set forth in the present disclosure can be negatively excluded from the methods and compositions of the present disclosure, and in particular from the claims of the present disclosure. In particular, the methods and compositions of the present disclosure can be free or essentially free of any component that is positively set forth in the present disclosure.

Other than in the operating examples, or where otherwise indicated, all numbers expressing quantities of ingredients and/or reaction conditions can be modified, if desired, with the term "about," meaning within +/−5% of the indicated number.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The terms "a," "an," and "the" are understood to encompass the plural as well as the singular. Thus, the term "a mixture thereof" is synonymous with "mixtures thereof." Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular method or composition includes both a nonionic surfactant and a fatty compound, a single fatty acid will serve as only the nonionic surfactant or as only the fatty compound (the single fatty acid does not serve as both the nonionic surfactant and the fatty compound).

All publications, patents, and patent applications cited in the present disclosure are herein incorporated by reference, and for any and all purposes, as if each individual publication, patent, or patent application were specifically and individually indicated to be incorporated by reference. In the event of an inconsistency between the present disclosure and any publications, patents, or patent applications incorporated herein by reference, the present disclosure controls.

The invention claimed is:

1. A method for providing broad spectrum photo-protection to skin, the method comprising topically applying to the skin a cosmetic composition comprising:
   (a) at least one antioxidant that boosts photo-protection from UVA radiation, the at least one antioxidant having:
      i. an Oxygen Radical Absorbance Capacity (ORAC) of at least 10,000 μmol TE/g; and
      ii. a Hydroxyl Radical Absorbance Capacity (HORAC) of at least 2,600 μmol GAE/g;
   (b) at least one organic UV filter; and
   (c) a cosmetically acceptable carrier;
      wherein the cosmetic composition provides an increase in $UVA_{PPD}$ PF of at least 30% relative to an otherwise identical cosmetic composition without the antioxidant(s) of (a);
      wherein the at least one antioxidant that boosts photo-protection from UVA radiation is selected from the group consisting of polydatin, phloretin, resveratrol, ferulic acid, their derivatives, and a mixture thereof; and
      the cosmetic composition is free of baicalin.

2. The method of claim 1, wherein the at least one antioxidant that boosts photo-protection from UVA radiation has a Superoxide Radical Absorbance Capacity (SORAC) of less than 200 U/mg.

3. The method of claim 1, wherein the at least one antioxidant that boosts photo-protection from UVA radiation is polydatin and the cosmetic composition provides an increase in $UVA_{PPD}$ PF of at least 150% relative to an otherwise identical cosmetic composition without the antioxidant(s) of (a).

4. The method of claim 1, wherein the at least one antioxidant that boosts photo-protection from UVA radiation is phloretin and the cosmetic composition provides an increase in $UVA_{PPD}$ PF of at least 50% relative to an otherwise identical cosmetic composition without the antioxidant(s) of (a).

5. The method of claim 1, wherein the at least one antioxidant that boosts photo-protection from UVA radiation is resveratrol and the cosmetic composition provides an increase in $UVA_{PPD}$ PF of at least 40% relative to an otherwise identical cosmetic composition without the antioxidant(s) of (a).

6. The method of claim 1, wherein the at least one antioxidant that boosts photo-protection from UVA radiation is ferulic acid and the cosmetic composition provides an increase in $UVA_{PPD}$ PF of at least 30% relative to an otherwise identical cosmetic composition without the antioxidant(s) of (a).

7. The method of claim 1, wherein the cosmetic composition comprises from 1 to about 35 wt. % of at least one organic UV filter, based on the total weight of the cosmetic composition.

8. The method of claim 1, wherein the total amount of antioxidant(s) of (a) is from about 0.01 to about 5 wt. %, based on the total weight of the cosmetic composition.

9. The method of claim 1, wherein the at least one organic UV filter of (b) is selected from the group consisting of selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof.

10. The method of claim 1, wherein the cosmetic composition comprises at least two organic UVB filters.

11. The method of claim 1, wherein the cosmetic composition is essentially free of inorganic UV filters.

12. The method of claim 1, wherein the total amount of organic UV filter(s) of (b) is from about 1 to about 40 wt. %, based on the total weight of the cosmetic composition.

13. The method of claim 1, wherein the cosmetically acceptable carrier comprises water.

14. The method of claim 13, wherein the cosmetically acceptable carrier further comprises at least one water-soluble solvent.

15. The method of claim 1, wherein the cosmetic composition comprises from about 40 to about 90 wt. % of the cosmetically acceptable carrier, based on the total weight of the cosmetic composition.

16. The method of claim 1, wherein the cosmetic composition further comprises:
   at least one solubilizing agent.

17. The method of claim 1, wherein the cosmetic composition further comprises:
   at least one emulsifier.

18. The method of claim 1, wherein the cosmetic composition further comprises:
   at least one silicone compound.

19. A method for providing broad spectrum photo-protection to skin, the method comprising topically applying to the skin a cosmetic composition comprising:
   (a) from about 0.01 to about 5 wt. %, based on the total weight of the cosmetic composition, of at least one antioxidant that boosts photo-protection from UVA radiation selected from the group consisting of polydatin, phloretin, resveratrol, ferulic acid, their derivatives, and a mixture thereof;
   (b) from about 1 to about 40 wt. %, based on the total weight of the cosmetic composition, of at least one organic UV filter; and
   (c) a cosmetically acceptable carrier comprising water and at least one water-soluble solvent or solubilizing agent;

wherein the cosmetic composition provides an increase in $UVA_{PPD}$ PF of at least 30% relative to an otherwise identical cosmetic composition without the antioxidant(s) of (a), and the cosmetic composition is free of baicalin.

* * * * *